US009081889B2

(12) United States Patent
Ingrassia, Jr. et al.

(10) Patent No.: US 9,081,889 B2
(45) Date of Patent: Jul. 14, 2015

(54) SUPPORTING THE MONITORING OF A PHYSICAL ACTIVITY

(75) Inventors: Michael I. Ingrassia, Jr., San Jose, CA (US); Eugene Dvortsov, San Francisco, CA (US)

(73) Assignee: Apple Inc., Cupertino, CA (US)

( * ) Notice: Subject to any disclaimer, the term of this patent is extended or adjusted under 35 U.S.C. 154(b) by 1209 days.

(21) Appl. No.: 12/943,852

(22) Filed: Nov. 10, 2010

(65) Prior Publication Data

US 2012/0116684 A1 May 10, 2012

(51) Int. Cl.
*G06F 19/00* (2011.01)

(52) U.S. Cl.
CPC .......... *G06F 19/3481* (2013.01); *G06F 19/321* (2013.01); *G06F 19/322* (2013.01)

(58) Field of Classification Search
USPC ..................... 702/19, 141, 177, 182, 183, 189
See application file for complete search history.

(56) References Cited

U.S. PATENT DOCUMENTS

| 7,198,607 | B2 | 4/2007 | Jamsen | |
|---|---|---|---|---|
| 7,334,472 | B2 | 2/2008 | Seo et al. | |
| 7,771,320 | B2 | 8/2010 | Riley et al. | |
| 2002/0013717 | A1 | 1/2002 | Ando et al. | |
| 2005/0060001 | A1* | 3/2005 | Singhal et al. | 607/19 |
| 2007/0271065 | A1* | 11/2007 | Gupta et al. | 702/160 |
| 2010/0185252 | A1* | 7/2010 | Bjorling et al. | 607/19 |

* cited by examiner

*Primary Examiner* — Mohamed Charioui
(74) *Attorney, Agent, or Firm* — Fish & Richardson P.C.

(57) ABSTRACT

Improved techniques and systems for utilizing a portable electronic device to monitor, process, present and manage data captured by a remote sensor during a physical activity session are disclosed. The portable electronic device offers a convenient user interface that can be visual and/or audio based customized to a particular application, user-friendly and/or dynamic. The portable electronic device can pertain to a personal media device and thus also provide media playback.

23 Claims, 11 Drawing Sheets

SUPPORTING THE MONITORING OF A PHYSICAL ACTIVITY

BACKGROUND

1. Field of the Embodiment

The presently described embodiments relate to personal media devices and, more particularly, to personal media devices that support user exercise routines.

2. Description of the Related Art

While most people appreciate the importance of physical fitness, many have difficulty finding the motivation required to maintain a regular exercise program. Some people find it particularly difficult to maintain an exercise regimen that involves continuously repetitive motions, such as running, walking and bicycling. Experienced athletes and trainers have found that feedback provides many people with motivation to maintain a regular exercise program. When a person can directly experience the results provided by an exercise program, that person typically will be encouraged to continue exercising. Recently the use of athletic information monitoring devices as represented by the Nike-iPod™ system has become commonplace. Typically, an athletic information monitoring device will incorporate a sensor for measuring parameters relating to the person being monitored and a portable computing device attached to or carried by the person for processing the parameters measured by the remote device.

A comprehensive system for supporting the monitoring an individual's physical activity is desired.

SUMMARY

The embodiments described relate to techniques and systems for utilizing a portable electronic device to monitor, process, present and manage data captured by a sensor. The portable electronic device offers a convenient user interface that can be visual and/or audio based customized to a particular application, user-friendly and/or dynamic. The portable electronic device can pertain to a personal media device and thus also provide media playback. Personal media device can take many forms that can include a personal media player (PMD) such as any member of the iPod™ family of portable media players including the iPod Touch, iPod Nano, and so on. In addition, personal media device can also take the form of a smart phone such as the iPhone™ all of which are manufactured by Apple Inc. of Cupertino, Calif.

The embodiments herein described can be implemented in numerous ways, including as a method, system, device, and computer readable medium. Several embodiments are discussed below.

In one embodiment, a method performed by a processor in a personal media device (PMD) for supporting and monitoring a physical activity is described. In one embodiment, the PMD includes at least a data storage device and a sensor arranged to detect an ambient activity, both the data storage device and the sensor being coupled to the processor. The method can be carried out by performing at least the following operations: generating ambient activity data in accordance with detected ambient activity by the sensor, receiving a starting trigger, the starting trigger causing the processor to initiate a physical activity session, receiving activity data from the sensor during the physical activity session; and processing the activity data and at least some recognized ambient activity data in a manner in accordance with the physical activity session.

In one aspect of the embodiment, at least one operation of the method is performed as part of a background operation of the processor.

A personal media device adapted for assisting a user during a physical activity session includes at least a processor and a sensor in communication with the sensor and arranged to detect an ambient activity and provide corresponding ambient activity data to the processor. The processor determines if at least some of the ambient activity data is recognized, responds to a starting trigger by starting a physical activity session and receiving physical activity data from the sensor during the physical activity session. The processor then processes at least some of the physical activity data and at least some recognized sensor data in a manner in accordance with the physical activity session.

In one aspect of the embodiment, the starting trigger takes the form of a sensor data pattern corresponding to a known starting trigger that operates to automatically start the physical activity session.

Non-transitory computer readable medium for storing computer code executable by a processor in a personal media device (PMD) for supporting and monitoring a physical activity is disclosed. In the described embodiment, the PMD includes at least a data storage device and a sensor arranged to detect an ambient activity each coupled to the processor. The computer readable medium includes computer code for generating ambient activity data in accordance with the ambient activity detected by the sensor, computer code for recognizing ambient activity data from the sensor, computer code for triggering a physical activity session, computer code for receiving physical activity data in accordance with the physical activity session, and computer code for processing at least some of the recognized ambient activity data and the physical activity data from the sensor in a manner in accordance with the physical activity session.

A system includes at least a portable electronic device that includes a processor, and a data storage device. The system also includes a sensor coupled to the processor and arranged to detect an ambient activity and provide corresponding ambient activity data to the processor. The processor evaluates the ambient activity data to determine if at least some of the ambient activity data is recognized and if at least some of the ambient activity data matches a data pattern corresponding to a trigger. When the trigger is a starting trigger, the processor causes the portable electronic device to initiate a physical activity session by processing physical activity data from the sensor and least some of the recognized ambient activity data in accordance with the physical activity session.

Other aspects and advantages of the embodiment will become apparent from the following detailed description taken in conjunction with the accompanying drawings which illustrate, by way of example, the principles of the embodiment.

BRIEF DESCRIPTION OF THE DRAWINGS

The embodiments herein described will be readily understood by the following detailed description in conjunction with the accompanying drawings, wherein like reference numerals designate like structural elements, and in which.

DETAILED DESCRIPTION OF REPRESENTATIVE EMBODIMENTS

Figure 1:
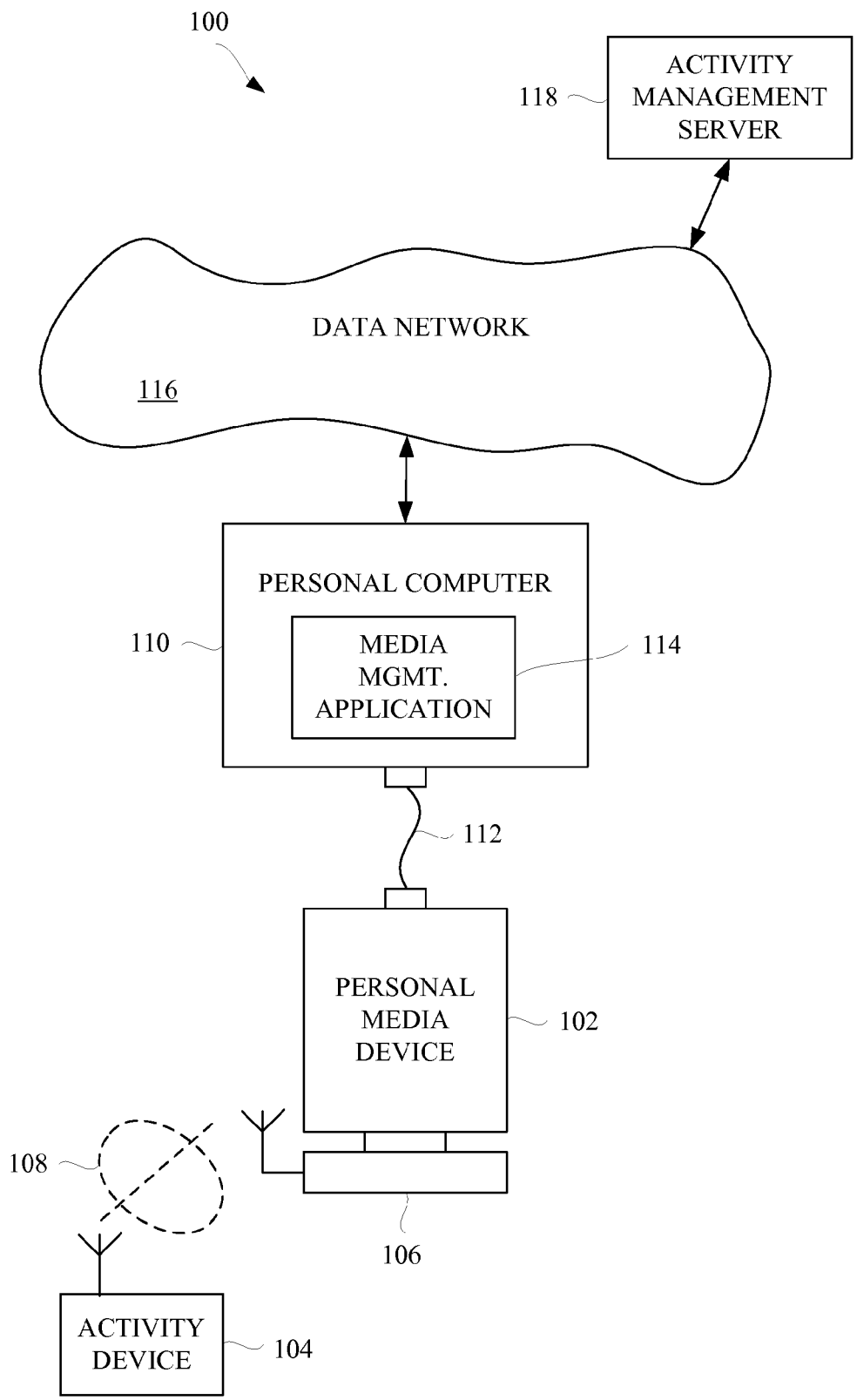
FIG. 1 is a block diagram of an activity monitoring system according to one embodiment of the embodiment.

In the following detailed description, numerous specific details are set forth to provide a thorough understanding of the concepts underlying the described embodiments. It will be apparent, however, to one skilled in the art that the described embodiments can be practiced without some or all of these specific details. In other instances, well known process steps have not been described in detail in order to avoid unnecessarily obscuring the underlying concepts.

Aspects of the described embodiments relate to the measurement, collection and display of activity related information such as athletic performance information. As will be appreciated by those of ordinary skill in the art, athletic information must first be obtained from an individual person. One or more different physiologic information monitoring devices can be used to measure and record physiologic data corresponding to the activity performed by the person. A physiologic information monitoring device can take many forms. In some cases the physiologic information monitoring device can include a sensor incorporated into a remote device for measuring parameters relating to the person being monitored and a computing device for processing the parameters measured by the sensor. The physiologic information monitoring device can also be configured to have most if not all sensors incorporated within or coupled directly to a housing of the physiologic information monitoring device. For example, an accelerometer and an RF device capable of receiving a GPS based transmission can be incorporated within the housing of the physiologic information monitoring device.

In any case, the parameters measured by the sensor can include parameters related to physical activity corresponding to athletic events such as running or jogging as well as the more commonplace activities such as walking, shopping, and so forth. The parameters can also include data such as calories burned, oxygen intake, body temperature, breathing rate, heart rate, and so forth. In some cases, the sensor can include geo-location functionality (such as GPS) that can geo-tag sensor data (i.e., provide metadata that can be used to tag or otherwise characterized data). For example, data provided by the sensor can be geo-tagged in such a way that the data can be correlated to a geographical location, elevation, and so forth.

The embodiments described relate to improved techniques and systems for utilizing a personal media device (PMD) to monitor, process, present and manage data captured by the sensing device (either remote or local). The PMD can pertain to a portable media device such as an iPod™, a personal communication device along the lines of the iPhone™, or portable computing platform such as a tablet computer that includes the iPad™, all of which are manufactured by Apple Inc. of Cupertino, Calif. More specifically, the sensor can be operable to monitor a person's activity. The activity can be related to specific athletic endeavors such as playing activity, working out, running, swimming, and so forth. The activity can also be related to physical activity that is not specifically directed at a particular athletic endeavor but nonetheless can be monitored in order to present a more complete picture of the person's overall physical activity level. In other words in addition to the specific athletic activities in which the person participates, the physical activity related to the person's ambient activities can also be monitored. For example, simply shopping can require a substantial amount of physical activity such as walking, climbing, lifting, and so on that can add to the person's overall daily physical activity load.

Sensing and storing physical activity data related to the ambient workout can enhance the overall view of the person's activity levels. Moreover, in some cases, it is desirable to use any of the previously stored ambient activity data to enhance the evaluation or presentation of a specific athletic endeavor, or workout. For example, when the person is walking and decides to jog or run, then an option can be presented that allows the previously stored walking data to be used as part of a trigger to indicate that a jogging or running workout has begun. Hence, a change in activity such as a stride change (a transition from one gait to another) can indicate a start or cessation of a workout session. From the example above, by changing stride from walking to jogging, the PMD can deduce that a jogging workout session has begun and modify the operation of the PMD accordingly. Of course, in order to distinguish a stride change indicative of a workout session from that unrelated to a workout session (such as running across the street), the PMD can monitor data received from the sensor in order to determine that the changed gait has been maintained for at least a predetermined amount of time. In this way, when the changed gait is maintained for at least the predetermined amount of time does the PMD conclude that the jogging workout session has begun and update the operating status of the PMD accordingly. Depending upon the outcome of the workout determination, the data associated with the jogging can be ignored (if determined to not be a workout session) or, otherwise, can be incorporated into the workout session evaluation. It should note as well that the cessation of the workout session can be identified by the stride change of jogging (or running) to walking or even completely stopping.

In some cases, it may be necessary to identify physical data as recognized physical activity (such as running, jogging, swimming, etc.) from physical activity that is not recognized as being specifically related to a particular workout regimen or physical activity. By using recognized physical activity data, the accuracy of the overall description of the person's physical activity can be improved since any irrelevant or unrelated data can be ignored. For example, if the person is preparing to swim laps in a pool, the physical activity related to walking to the pool side is likely to not be recognized as being related to that physical activity of swimming laps. However, if there is a pattern of activity that identifies swimming laps that includes the walking to the poolside, then the walking data can be used to not specifically characterize the swimming laps workout but rather to indicate (or confirm) that the swimming workout is about to start and therefore the sensor should be prepared to receive data related to swimming laps (such as lap time based upon an accelerometer data indicating a kick turn along with temporal data from an on board timer).

Therefore, the ability to quickly and accurately identify a pattern of activity data (also referred to as an activity data profile, or more simply activity profile) as a particular workout or physical activity can be very useful since it at least allows for a more hands off approach to monitoring a physical activity. For example, when a processor in the PMD recognizes a particular pattern of behavior and that recognized pattern of behavior has a workout template associated with it, then the processor can begin executing instructions included in the workout template without user intervention. In addition to using physical activity data to provide a basis for recognition, other physical parameters can also be used singly or in combination with each other to identify a particular physical activity is either about to begin or has already begun. In the latter case, if the physical activity has already begun, then it may be desirable to incorporate previously stored ambient data related to the identified physical activity into the overall analysis of the identified physical activity. Parameters such a location, time, context of use, and so forth can be compared to data patterns that correspond to specific physical activities. When, for example, the sensor data includes location data, time of day data, and elevation change data and so forth, the sensor data can be compared to known or at least estimated data patterns corresponding to a known physical activity. Depending upon a degree of match, or correlation, between the sensor data and the data patterns, an estimate of the current physical activity can be made.

It should also be noted that a workout session can be initiated (or stopped) by way of a single event, such a single input event. The single input event can take many forms. The single input event can be as simple as a single input event such as click or a touch at an appropriately sensitive user interface. The single input event can also take the form of a gesture such as a finger swipe on a touch sensitive display or input pad, or even shaking the PMD in a "shake to start" or "shake to stop" operation. In addition to input events along the lines described, the single input event can also take the form of a connection event related to the coupling of an external circuit (such as a heart rate monitor, or HRM, workout equipment such as a treadmill) that can trigger an "auto-start" process used to automatically begin an associated workout session.

In a particular example, a single input event (such as pressing a button on a remote sensor) can cause an auto-start routine to execute at least the following operations automatically:
 1) Start a timer,
 2) Start recording data,
 3) Set music to shuffle, and
 4) Pair to HRM and Shoe sensor in real time (on the fly).
In addition to triggering the start of a workout session, a pattern of behavior can also be used to indicate at least an end of a workout session, or in some cases, a pause in the workout session. For example, if the PMD detects that a motion parameter, such as an indication of an instantaneous pace has been about zero for a pre-set amount of time (say, for example, about 1 minute) and/or that the HRM indicates that the heart rate has decreased to below a threshold, the PMD can stop or at least pause the workout automatically without explicit user interaction.

If sensor data includes an indication that the local environment is outdoors (by the presence of ambient light having a frequency spectrum, color temperature, etc. that matches that of sunlight), then location data and motion data having elevation changes and relatively constant speed in a range consistent with jogging can be resolved by the processor to indicate that the person is likely jogging outdoors. It should also be noted, however, that in some cases accelerometer data can assist in determining the type of ongoing activity. For example, while the speed may be constant (in terms of how fast the individual is jogging), the accelerometer data profile will have varying speeds based on where we are in the step of the run. For instance, on a bike, the accelerometer data profile can exhibit more abrupt speed changes due to the bicycle itself presenting an accelerometer data profile specific to bike riding.

It should be noted that there are many ways to automatically determine whether the sensor is outdoors or indoors. One technique can be well suited by personal media devices having image capture resources such as a camera (either front facing or rear facing or both). These image capture resources can be used to periodically capture ambient light (by simply the processor enabling the image capture device and capturing an ambient light sample) that can then be resolved for color temperature, frequency spectrum, and so forth. In this way, the outdoors/indoors data can be stored for later use in determining if a particular ensemble of physical activity data correlated to a known physical activity and if so, identify the physical activity.

When it is determined that it is likely that the sensor is outdoors, then an outdoor jogging workout profile, or template, can be used to provide an appropriate outdoor jogging workout. On the other hand, when the color temperature, frequency spectrum, and so forth is more akin to that expected from indoor lighting (tungsten, fluorescent lighting), then any elevation change can be ascribed to climbing stairs indoors. It should be noted, however, that in some cases an indication of artificial light may not always indicate an indoor environment. For example, if the color temperature, frequency spectrum is associated with mercury vapor, or sodium based lighting, then it is more likely than not that the physical activity is taking place outdoors at night in the presence of illuminated street lamps.

In addition to ambient lighting, other data can be used to determine if the local environment is indoors or outdoors. For example, when the sensor is equipped to receive RF signals such as those associated with GPS, cell phones, Bluetooth and so forth, then the relative strength of the RF signal can be used to evaluate if the local environment is indoors or outdoors. RF signal strength indicating a strong GPS signal is more likely to be associated with a clear view of the sky and therefore likely to be associated with the outdoors. Of course, if the sensor was located in an interior space having a direct view of the sky, other factors such as ambient lighting, if any, RF signal strength of cellular telephone base stations, the presence of RF signals related to short range wireless protocols such as Bluetooth, and any other external factor can all be used in any combination to arrive at an estimate whether or not the sensor is indoors or outdoors.

In any case, the processor can use any data that can be reasonably associated with a particular physical activity in order to more accurately identify, or recognize, a physical activity and once identified provide an appropriate workout template for processing the physical activity data.

In one embodiment, the PMD can also either directly support wireless communication with the remote sensor or indirectly support wireless communications by using an attachable accessory device that provides wireless capability to the portable electronic device. The embodiments herein described are particularly well suited for use in monitoring activity-related data, such as exercise data (e.g., run data). However, it should be recognized that the described embodiments are not limited to activity monitoring, but instead is applicable to any type of monitoring. For example, the monitoring can be any physiological monitoring of a person, who is typically the user of a portable electronic device.

One aspect of the described embodiments is evaluation of an individual's ambient activity to determine if the ambient activity can be identified as a recognized physical activity. The evaluation can also determined if data associated with the ambient activity can be used in the evaluation of a recognized physical activity. Furthermore, the ambient activity data can be used to provide a more accurate assessment of the individual's overall physical activity. For example, simply walking upstairs can be considered ambient activity unrelated to a specific athletic endeavor. However, when considered as part of the individual's overall physical activity, stair climbing can in reality represent a not insubstantial part of an individual's overall physical activity. However, not all ambient activity can or should be considered to be part of the individual's overall physical activity. For example, detecting accelerated motion of the individual can be related to relevant physical activity such as running and/or jumping. On the other hand, the detected acceleration can in fact be related to irrelevant physical activity such as sitting down or standing up. Therefore, in order to more accurately evaluate the individual's ambient activity and to therefore provide a more accurate determination of the contribution of the individual's ambient workout to the overall physical activity, techniques for recognizing relevant physical activity from irrelevant physical activity can be employed.

In order to avoid considering actions that mimic physical activity, techniques for recognizing and categorizing detected activity can be employed to store data related to only those activities that contribute to the individual's overall physical effort. Accordingly, one aspect of the described embodiments is organization of data monitoring and management into workouts. Another aspect is a graphical user interface that permits user configuration or user selections, presents menus for workout selection, presents workout status information, and provides workout results. Still another aspect of the embodiment is use of templates to describe characteristics of workouts. Yet still another aspect of the embodiment is playing a designated playlist (i.e., a group of songs) during a workout. Still yet another aspect of the embodiment is near immediate playback a particular predetermined media item (e.g., song) on-demand (e.g., requested by a predetermined user interface action or by system based on workout monitoring) and disregarding any other media item being otherwise played. These aspects and various others discussed herein can be used separately or in any combination.

In addition to detected physical activity acting as a trigger to initiate a physical activity session or at least a physical activity data logging operation, the triggering event can include the act of merely connecting the sensor to the personal media device. For example, the act of connecting a heart rate monitor to the personal media device (and/or the personal media device recognizing that the heart rate monitor has been connected) can act as the trigger (or at least one of the triggers) to initiate a cardio type workout. In this way, once the cardio type workout has been triggered, workout templates, previously stored workout data, associated playlists, and so forth can be retrieved automatically without requiring the user to do anything more than connect the sensor to the personal media device.

In another embodiment, connecting the personal media device and/or sensor to an electronic workout apparatus such as a treadmill can initiate a process whereby the electronic workout apparatus receives a workout template. The workout template can include specifically configured workout routine (time, speed, elevation, and so forth) specially designed for the user. In addition, data can be received from the electronic workout apparatus. The data can include information related to distance run, elevation climb, and so forth that can be used to assess the user's performance. The information from the electronic workout apparatus can also be used in conjunction with physiometric data received from the sensor to provide a more complete and accurate assessment of the workout.

In addition to receiving physiometric data from the sensor, the personal media device can provide feedback to the user in the form of voice feedback, visual feedback, audible feedback, or music feedback. The feedback can be used to help the user improve the current workout, provide a virtual coach that can prompt the user to improve the workout, and so forth.

Embodiments are discussed below with reference to FIGS. 1-9A/9B. However, those skilled in the art will readily appreciate that the detailed description given herein with respect to these figures is for explanatory purposes as the described embodiments extends beyond these limited embodiments.

FIG. 1 is a block diagram of activity monitoring system 100 according to one embodiment of the embodiment. Activity monitoring system 100 can be an electronic system that enables activity related information to be acquired, stored, analyzed, presented and shared. In some embodiments, activity monitoring system 100 can include personal media device 102. Personal media device 102 can be capable of storing data and processing the stored data. For example personal media device 102 can store and play media data. In other words, personal media device 102 can output (e.g., play) audio and/or video. Activity monitoring system 100 can also include sensor 104. Sensor 104 can relate to conditions of a local environment that can be detected by sensor 104. For example, conditions of the local environment can be related to a physical location of sensor 104, physical motion and/or acceleration of sensor 104 and so forth. In this regard, sensor 104 can detect, for example, a geographical location using GPS, cellular transmission triangulation techniques, and so on whereas an accelerometer, a gyroscope, etc. can be used to detect motion, rotation, and so forth. In other aspects, sensor 104 can also detect physiometric activity of the individual. The physiometric activity can include at least a heart rate (HR), a breathing rate (BR), body temperature and so on.

Sensor 104 can also include wireless transmission capability so that the activity related data can be transmitted to personal media device 102. In particular, personal media device 102 includes a wireless interface accessory 106. The wireless interface accessory 106 includes a wireless transceiver so that the wireless interface accessory 106 can receive the activity related data being transmitted by sensor 104 by way of a wireless connection through a personal wireless network 108. Personal media device 102 can receive the activity related data from sensor 104 via the wireless interface accessory 106 and can then operate to process and store the activity related data at personal media device 102.

The activity monitoring system 100 also includes a computing system 110. Computing system 110 can take many forms. Computing system 110 can take the form of a personal computer such as a laptop computer, desktop computer, and tablet computing device such as the iPad™. Personal media device 102 can be electrically connected to the computing system 110 by way of a cable 112 or by way of a wireless communication channel. The cable 112 can, for example, be a Firewire or USB cable. Alternatively, the cable 112 can be replaced with a wireless link. Although personal media device 102 is not normally electrically connected to the computing system 110, the electrical connection when present facilitates information exchange between personal media device 102 and the computing system 110.

The computing system 110 includes a media management application 114. The media management application 114, in one embodiment, can not only manage the media assets stored on the computing system 110, but can also store and manage activity related data. In one embodiment, the media management application 114 can operate to cause the activity related data stored on personal media device 102 to be copied to the computing system 110. Thereafter, the activity related data can be analyzed at the computing system 110 and/or made available to the user of the computing system 110. In addition, the activity monitoring system 100 can facilitate the computing system 110 coupling to a data network 116. The data network 116 can represent a global or Wide Area network, such as the World Wide Web (or the Internet). When the computing system 110 is coupled to the data network 116, the activity related data present at the computing system 110 can be transferred to an activity management server 118. At activity management server 118, the activity related data can be further analyzed and/or processed to facilitate usefulness of the data. Activity management server 118 supports storage and analysis of activity related data from a large number of different personal media devices and/or personal computers. Hence, activity management server 118 can also compare the activity related data from different users. Activity management server 118 can also provide a website that can be accessed by a network browser operating on the computing system 110 or other computing device to access activity related information or other information made available via the website. Sensor 104 illustrated in FIG. 1 can take a variety of different forms. In one embodiment, the activity device is a sensor-based device. One example of a sensor-based device is a pedometer. Another example of the sensor-based device is a heart rate monitor.

Figure 2:
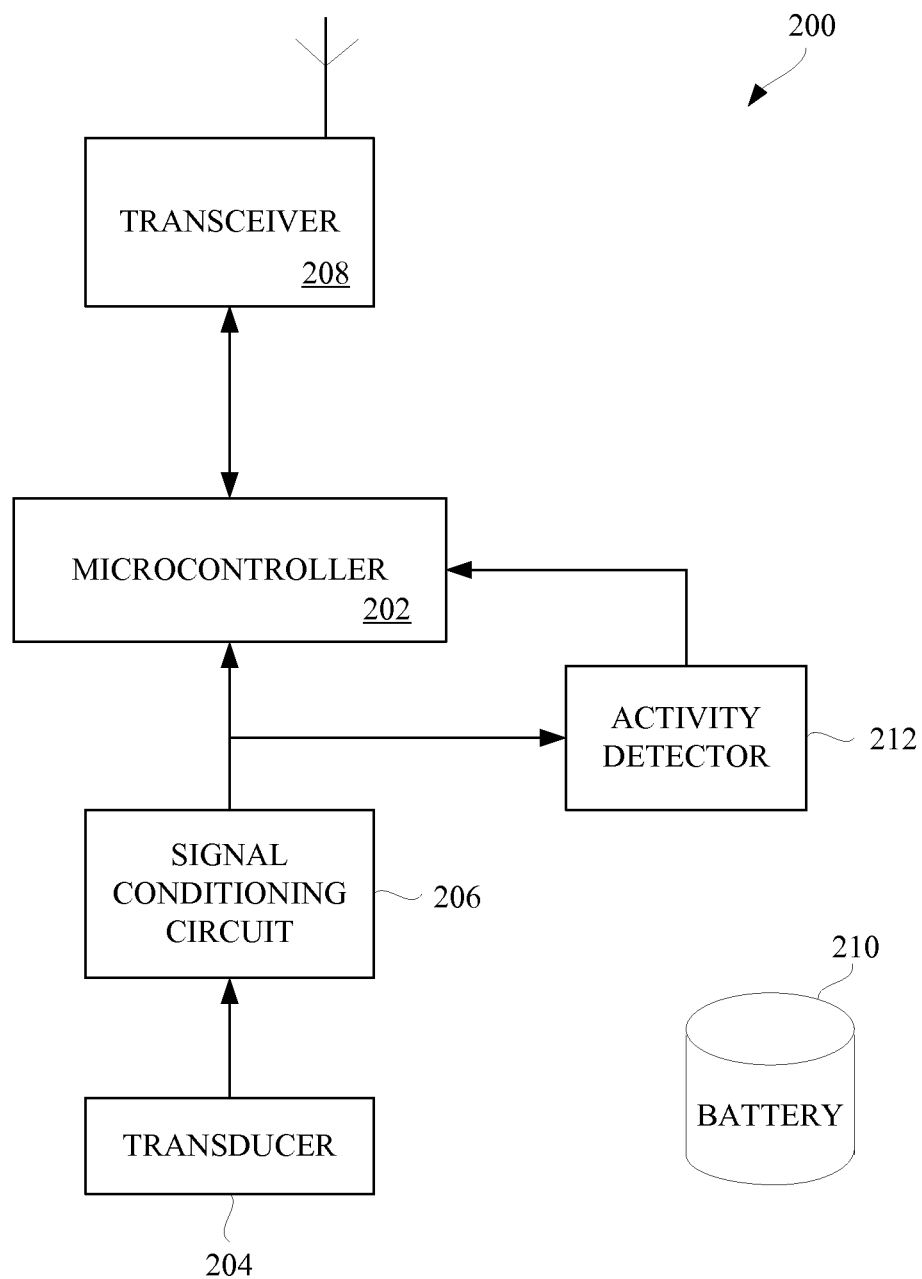
FIG. 2 illustrates a block diagram of an activity device according to one embodiment of the embodiment.

FIG. 2 illustrates a block diagram of an activity device 200 according to one embodiment of the embodiment. Activity device 200 is, for example, suitable for use as sensor 104 illustrated in FIG. 1. Activity device 200 includes a microcontroller 202 that controls the overall operation of activity device 200. Activity device 200 also includes a transducer 204 that acquires raw activity data. As an example, the transducer 204 can pertain to a piezo-electric device (e.g., piezo-electric pedometer). With a piezo-electric device, electrical signals associated with pressure applied to the transducer 204 are produced as a user of activity device 200 walks or runs. In one embodiment, activity device 200 can be embedded within a shoe, such as within a sole of a shoe. In another embodiment, activity device 200 can be strapped on and worn to be able to monitor the user's cardiac activity. In still other embodiments, activity device 200 can be incorporated into a garment worn by the user. A signal conditioning circuit 206 filters and/or amplifies the raw activity data supplied by the transducer 204. The resulting conditioned activity data is then supplied to the microcontroller 202. The microcontroller 202 includes memory that can store the conditioned activity data. Activity device 200 also includes a transceiver 208 to transmit the conditioned activity data to a personal media device, such as personal media device 102 via the wireless interface accessory 106 illustrated in FIG. 1. Since activity device 200 need not receive data back from personal media device 102, the transceiver 208 can alternatively be a transmitter.

Still further, activity device 200 is battery powered by battery 210. In one embodiment, battery 210 is not replaceable by the user of activity device 200. Accordingly, activity device 200 is designed to operate in a low power manner. In this regard, the microcontroller 202 is a low power design and can be placed in a sleep/hibernate mode when activity data is not being acquired. In one embodiment, activity device 200 includes an activity sensor 212. The activity sensor 212 can monitor the transducer 204 or the signal conditioning circuit 206 to determine whether the activity data is indicating that there is some physical related activity (e.g., running, walking, etc.) being undertaken. When the activity sensor 212 determines that there is no physical related activity, the activity sensor 212 can cause or signal the microcontroller 202 to enter a low power mode (i.e., sleep or hibernate). When the activity sensor 212 determines that there is physical related activity while the microcontroller 202 is in the low power mode, the activity sensor 212 can cause or signal the microcontroller 202 to awaken to a normal mode.

Figure 3:
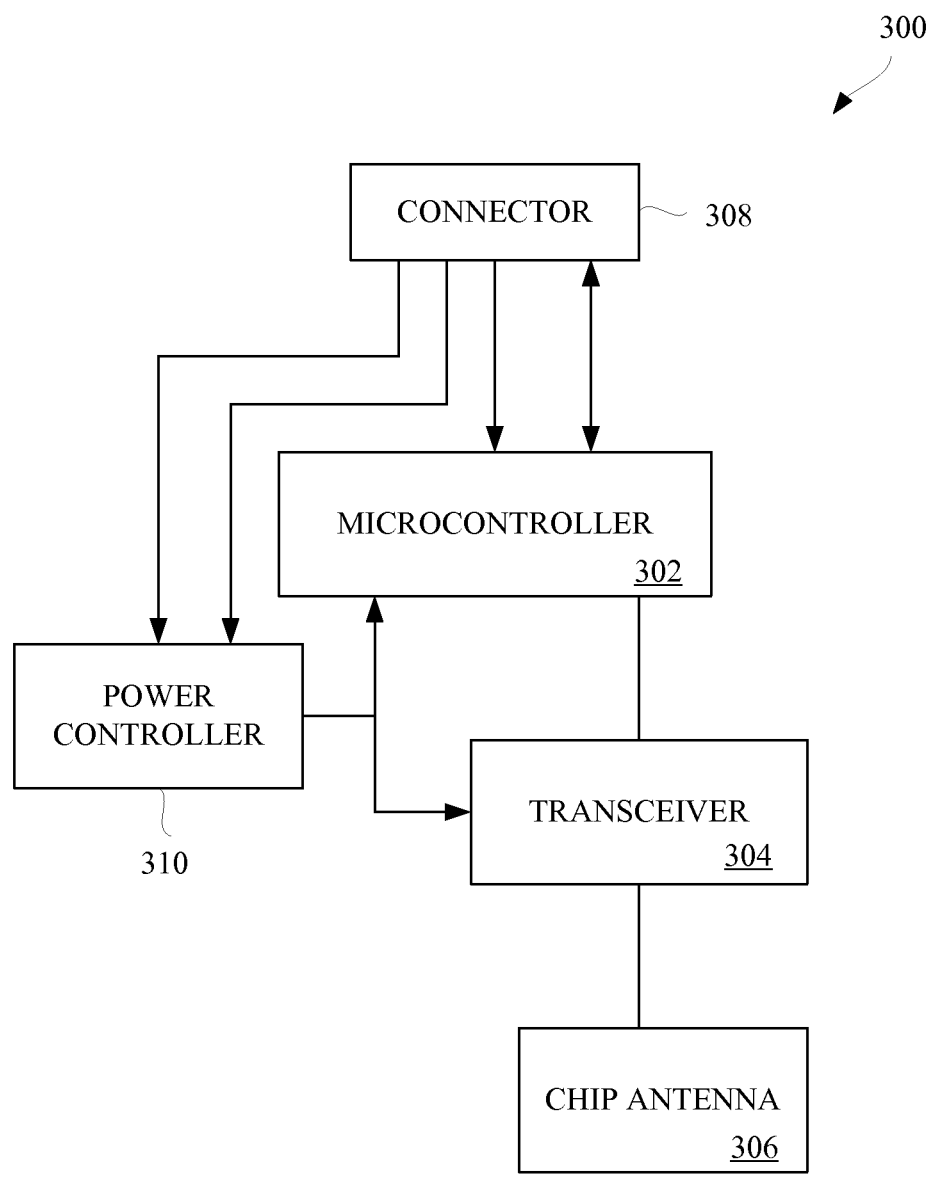
FIG. 3 is a block diagram of a wireless interface accessory according to one embodiment of the embodiment.

FIG. 3 is a block diagram of a wireless interface accessory 300 according to one embodiment of the embodiment. The wireless interface accessory 300 is, for example, suitable for use as the wireless interface accessory 106 illustrated in FIG. 1. The wireless interface accessory 300 includes a microcontroller 302 that controls the overall operation of the wireless interface accessory 300. The wireless interface accessory 300 also includes a transceiver 304 and a chip antenna 306. The transceiver 304 operates to wirelessly communicate with the counterpart device, such as an activity device, to receive activity related data. Activity related data is then temporarily stored in memory provided with the microcontroller 302 and then forwarded to a personal media device via a connector 308. The connector 308 can couple with a counterpart connector associated with personal media device. The microcontroller 302 can also store some user data, including calibration data, as well as activity data, including data summaries, workout data, etc. The wireless interface accessory 300 can also include power controller 310. The power controller 310 couples to a power source and ground from the connector 308. The power controller 310 typically converts the incoming voltage level to a different voltage level to be utilized by the microcontroller 302 and the transceiver 304.

Figure 4A:
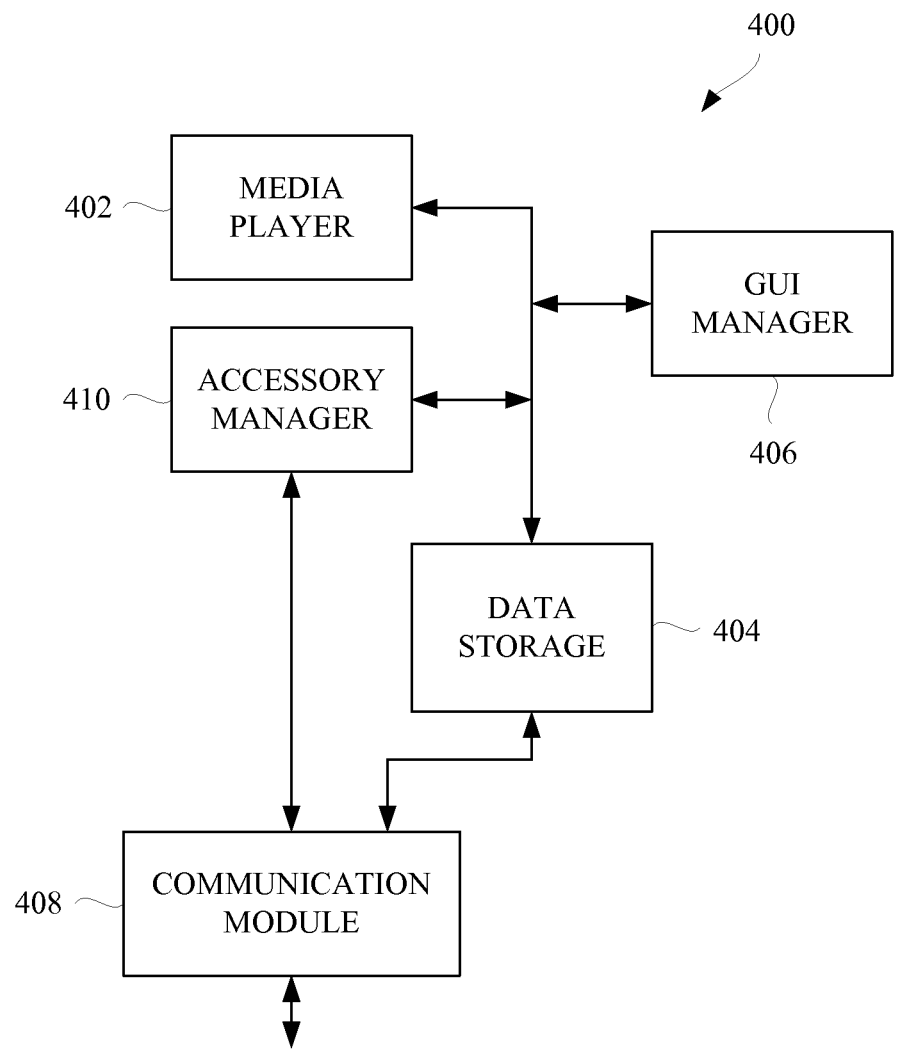
FIG. 4A is a block diagram of an arrangement of functional modules utilized by a personal media device.

FIG. 4A is a block diagram of an arrangement 400 of functional modules utilized by a personal media device. Personal media device can, for example, be personal media device 102 illustrated in FIG. 1. The arrangement 400 includes a media player 402 that is able to output media for a user of personal media device but also store and retrieve data with respect to data storage 404. The arrangement 400 also includes a graphical user interface (GUI) manager 406. The GUI manager 406 operates to control information being provided to and displayed on a display device. The arrangement 400 also includes a communication module 408 that facilitates communication between personal media device and an accessory device. Still further, the arrangement 400 includes an accessory manager 410 that operates to authenticate and acquire data from an accessory device that may be coupled to personal media device. For example, the accessory device can be a wireless interface accessory, such as the wireless interface accessory 106 illustrated in FIG. 1 as being coupled to personal media device 102.

Figure 4B:
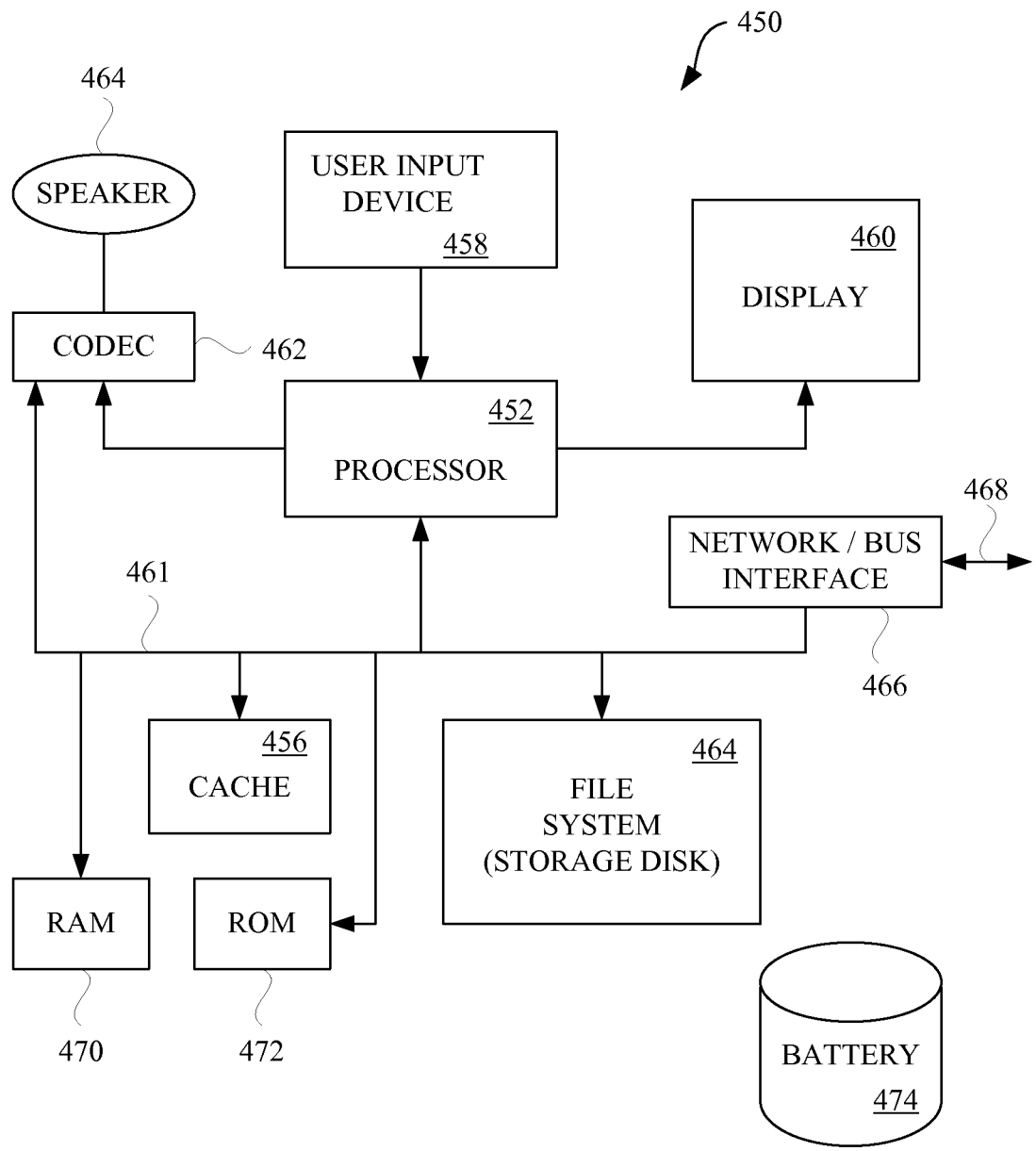
FIG. 4B is a block diagram of a media player suitable for use with the described embodiments.

FIG. 4B is a block diagram of a media player 450 suitable for use with the described embodiments. Media player 450 illustrates circuitry of a representative personal media device. Media player 450 includes a processor 452 that pertains to a microprocessor or controller for controlling the overall operation of media player 450. Media player 450 stores media data pertaining to media items in a file system 454 and a cache 456. The file system 454 is, typically, a storage disk or a plurality of disks. The file system 454 typically provides high capacity storage capability for media player 450. However, since the access time to the file system 454 is relatively slow, media player 450 can also include a cache 456. The cache 456 is, for example, Random-Access Memory (RAM) provided by semiconductor memory. The relative access time to the cache 456 is substantially shorter than for the file system 454. However, the cache 456 does not have the large storage capacity of the file system 454. Further, the file system 454, when active, consumes more power than does the cache 456. The power consumption is often a concern when media player 450 is a personal media device that is powered by a battery 474. Media player 450 also includes a RAM 470 and a Read-Only Memory (ROM) 472. The ROM 472 can store programs, utilities or processes to be executed in a non-volatile manner. The RAM 470 provides volatile data storage, such as for the cache 456.

Media player 450 also includes a user input device 458 that allows a user of media player 450 to interact with media player 450. For example, the user input device 458 can take a variety of forms, such as a button, keypad, dial, etc. Still further, media player 450 includes a display 460 (screen display) that can be controlled by the processor 452 to display information to the user. A data bus 461 can facilitate data transfer between at least the file system 454, the cache 456, the processor 452, and the CODEC 462.

In one embodiment, media player 450 serves to store a plurality of media items (e.g., songs, podcasts, etc.) in the file system 454. When a user desires to have the media player play a particular media item, a list of available media items is displayed on the display 460. Then, using the user input device 458, a user can select one of the available media items. The processor 452, upon receiving a selection of a particular media item, supplies the media data (e.g., audio file) for the particular media item to a coder/decoder (CODEC) 462. The CODEC 462 then produces analog output signals for a speaker 464. The speaker 464 can be a speaker internal to media player 450 or external to media player 450. For example, headphones or earphones that connect to media player 450 would be considered an external speaker. Media player 450 also includes a bus interface 466 that couples to a data link 468. The data link 468 allows media player 450 to couple to a host device (e.g., host computer or power source). The data link 468 can also provide power to media player 450.

Media player 450 also includes a network/bus interface 466 that couples to a data link 468. The data link 468 allows media player 450 to couple to a host computer or to accessory devices. The data link 468 can be provided over a wired connection or a wireless connection. In the case of a wireless connection, the network/bus interface 466 can include a wireless transceiver. The media items (media assets) can pertain to one or more different types of media content. In one embodiment, the media items are audio tracks (e.g., songs, audiobooks, and podcasts). In another embodiment, the media items are images (e.g., photos). However, in other embodiments, the media items can be any combination of audio, graphical or video content.

Figure 5:
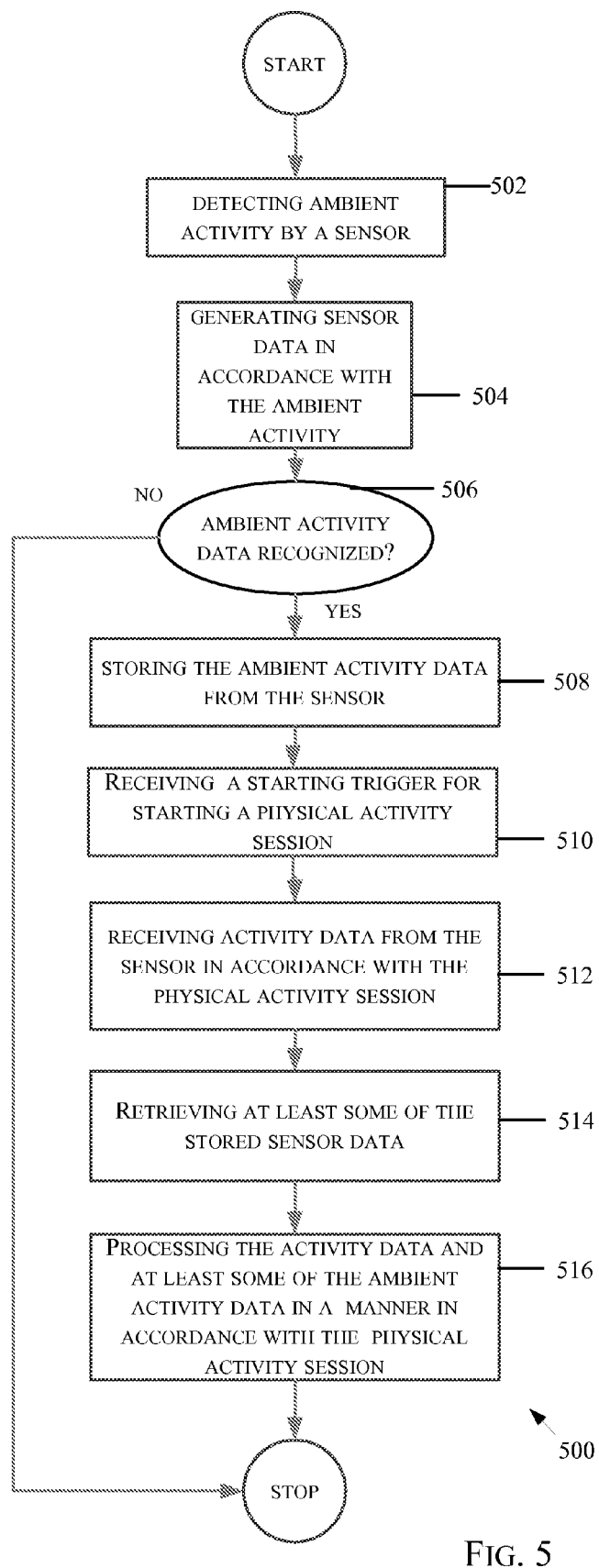
FIG. 5 is a flow chart describing a process in accordance with the described embodiments.

FIG. 5 is a flow diagram of process 500 according to one embodiment of the embodiment. The process 500 is, for example, performed by a computing device, typically a portable computing device. For example, the computing device can be a personal media device, such as personal media device 102 illustrated in FIG. 1. The personal media device can be connected to or at least in communication with a sensor arranged to detect an ambient activity. The ambient activity can take many forms. For example, when the sensor is worn by a user, the sensor can detect physiometric data such as a heart rate, body temperature, breathing rate, and so forth. The sensor can also include motion detection functionality, location detection functionality, an accelerometer, light capture device, and so on.

Accordingly process 500 initially detects ambient activity by the sensor at 502. For example, when the sensor is worn by the user and the user is walking, then the sensor can detect that the user is walking by correlating various motion and acceleration measurements based upon a model that has been calibrated for walking. Next, at 504 as the sensor continues to detect the ambient activity, the sensor is generating ambient activity data in a form that can be processed by the processor and/or stored in a memory device. At 506, the processor can process the ambient activity data in order to determine whether or not the ambient activity is recognized or not. In one embodiment, the processor can compare the received ambient activity data to a data pattern of a known recognized physical activity described in more detail as process 600 described below. In other words, the received ambient activity data is processed in such a way so as to form a data pattern corresponding to the ambient activity data that is then compared to the data pattern of the known recognized physical activity. If the processor determines that there is no match, or at least that degree of matching is not sufficient to indicate a full match, then the process 500 ends. It should be noted, however, that in some embodiments, the unrecognized stimulus activity data is stored for potential subsequent processing.

When at 506, the ambient data is recognized, and then the recognized ambient data is stored in a memory device at 508. It should be noted that steps 502-508 operate in the background and require no user intervention. In this way, ambient activity data is being continuously received, evaluated and stored if necessary. However, in order to not overload the memory resources, a particular implementation can require that only a specific amount of memory resources be used to store ambient activity data. For example, memory resources corresponding to 10 minutes worth of ambient data can be stored after which the previously stored data is overwritten by more recent data. In this way, the user has access to what is most likely the most relevant ambient activity data.

At 510, a physical activity session is started when a starting trigger is received. In the described embodiment, the activity session can relate to a specific workout such as running, swimming, jogging, and so forth. In some cases the starting trigger can be a user initiated event received from the user by way of the portable media device using, for example, a user interface. The user interface can be a graphical user interface presented on a display or the user interface can take the form of a switch or switches, input connections, and so forth for those personal media devices that do not possess a display. In other cases, however, the starting of the physical activity session can be initiated automatically based upon the recognition of the ambient activity, or a combination of the ambient activity and other external factors such as location, temperature, and so forth. In this situation, the recognition of the ambient activity can trigger the physical activity session. For example, when the user starts to jog or run, the personal media device can recognize the physiometric data associated with running (velocity change, heart rate change, stride length change, and so on) to automatically retrieve a workout template (that can include a playlist, for example) corresponding to a running workout.

At 512, activity data in accordance with the recognized physical activity is received from the sensor and at 514, at least some of the stored ambient activity data is retrieved. Next at 516, at least some of the stored ambient data and the activity data is processed in a manner in accordance with the physical activity session. For example, when the ambient data is associated with walking that develops into a jog and then into run, although the run is the trigger that initiates the running workout, the walking and jogging data can add to the overall evaluation of the running workout. Furthermore, when the ambient data changes back from running to jogging to walking, this change in data can indicate that the running workout is complete that can act as a trigger to end the running workout.

Figure 6:
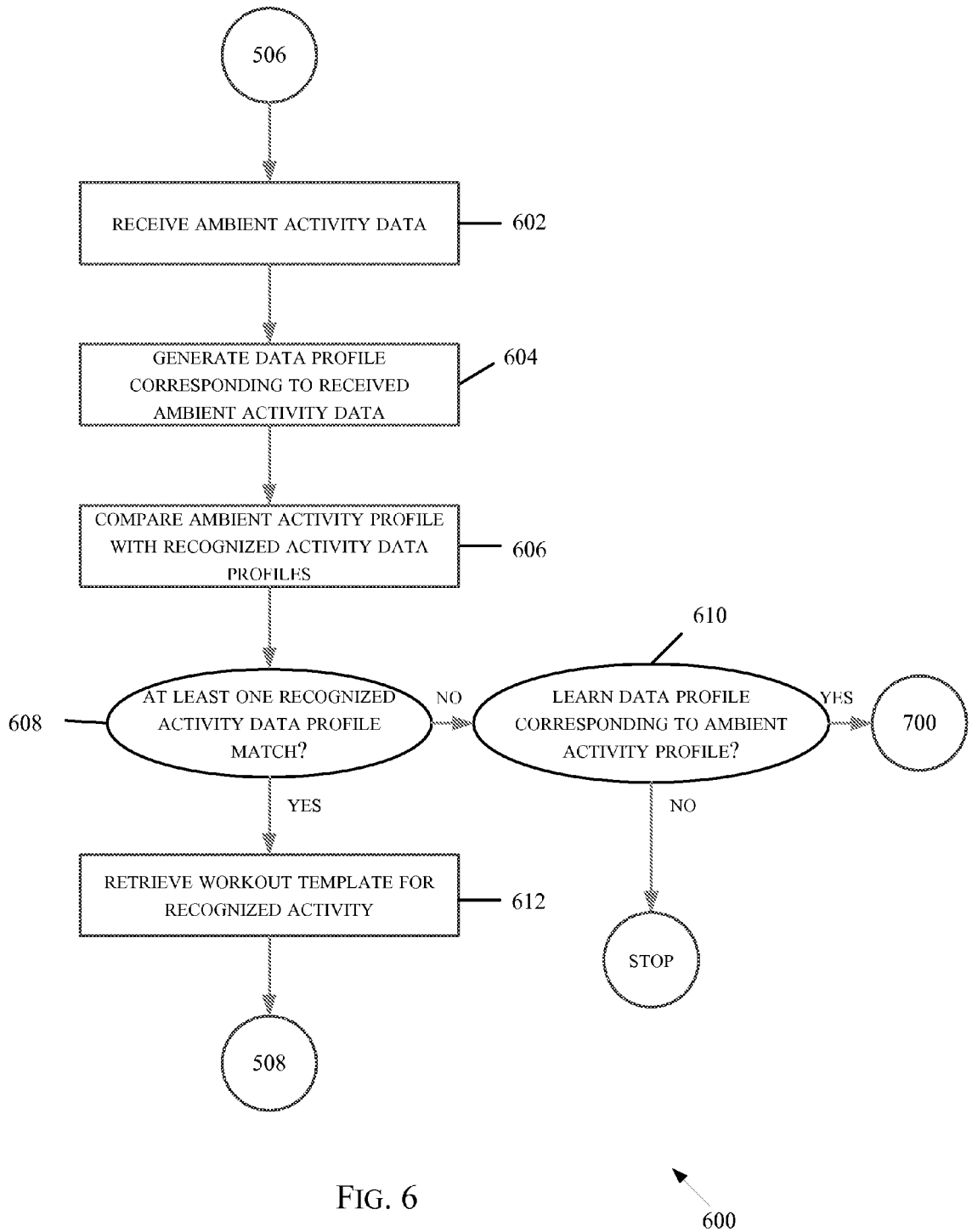
FIG. 6 is a flow diagram of a recognizing process according to one embodiment of the embodiment.

FIG. 6 is a flow diagram of process 600 that can be used to recognize ambient activity data according to one embodiment of the embodiment. The process 600 is, for example, performed by a computing device, typically a portable computing device. For example, the computing device can be a personal media device, such as personal media device 102 illustrated in FIG. 1.

Process 600 initially receives at 602 ambient activity data. The ambient activity data can be received from the sensor directly or from a memory device in which at least some of the ambient activity data is stored. In some cases, this step can involve user interaction with the computing device to select or enter information that leads to determination if the process 600 is to proceed. This can be useful in those situations where power resources are limited such as for a battery powered device having a limited remaining battery charge. This intervention may be particularly suitable since process 600 typically runs in the background unnoticed by the user. Process 600 can then proceed to 604 where the processor uses the received ambient activity data to generate a data profile. The data profile can be generated using a data profile generator that can be implemented in software and executed by the processor. In one embodiment, the data profile generator can categorize the ambient activity data based upon particular activity signatures that can correspond to specific activities. The activity signature can then be used to compare with known, or recognized, activity data profiles in 606 where the ambient activity signature is compared to at least one recognized activity data profile. In this case, depending upon the degree of matching, process 600 can indicate that the ambient activity data corresponds to a known, or recognized, activity data profile.

For example, when the ambient activity data includes motion data indicative of a speed corresponding to jogging (say, for example, 4-8 mph) and an indication of repeated intervals of jogging speed interspersed with walking speed, then the data profile generator can identify the ambient activity data as interval training. In some cases, the data profile generator can assign a probability to the data profile (or profiles). This can be particularly useful when the ambient activity data is somewhat ambiguous or does not readily fit pre-established activity models.

Therefore, if at 608 there are no matching recognized activity data profiles, then process 600 proceeds to 610 where a learning option can be invoked. In some embodiments, whether or not the learning option is invoked can be pre-determined by the user by way of a user interface either during a setup operation or in real time. If is determined that learning option is not available, or not selected, then process 600 stops and no further action is taken for processing any already received ambient activity data. On the other hand, if it is decided that the learning option is available and is to be used to learn the heretofore unrecognized ambient activity data, then process 600 proceeds to learning process 700 described below.

Turning back to 608, if at least one recognized activity data profile matches (or matches close enough) to be considered recognized, then at 612 a workout template corresponding to the recognized activity is retrieved in preparation for initiating a workout session. It should be noted that process 600 can run in the background without real time user intervention. The workout templates can be used to define workouts. A workout template can characterize or describe a workout. A template can, for example, be provided as a XML file. The templates can be included in firmware of the portable electronic device, such as the portable media device 102, or downloaded to the portable electronic device.

Figure 7:
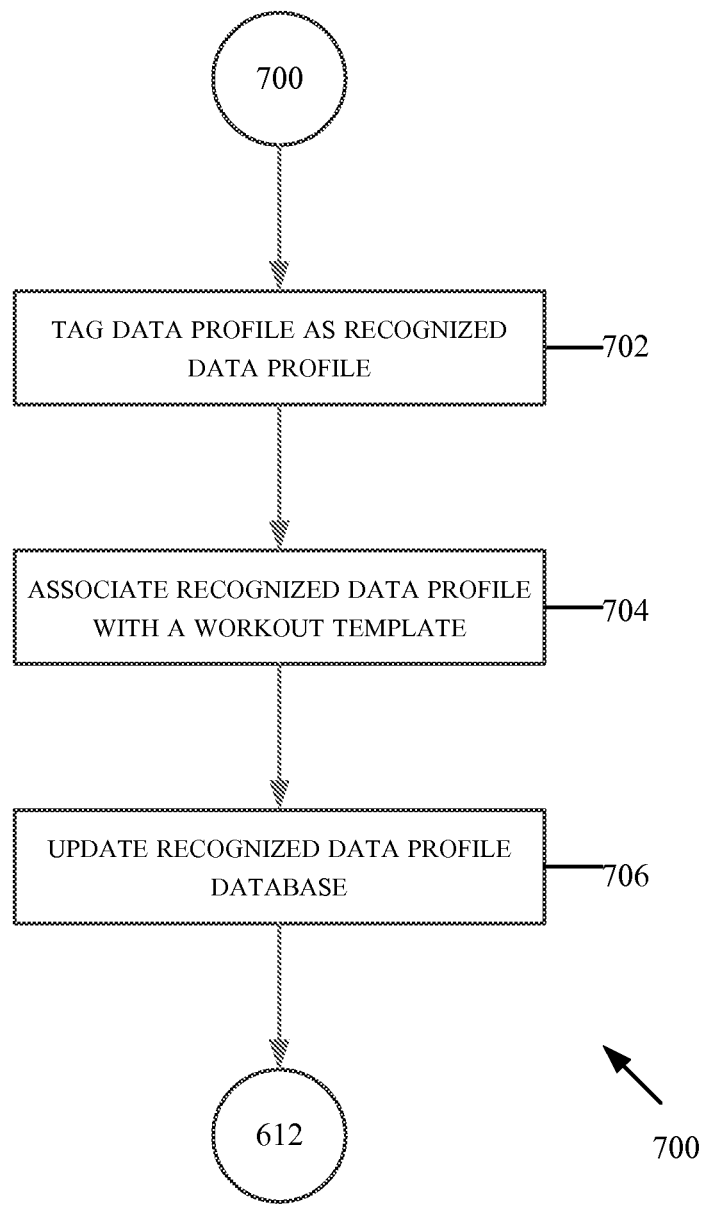
FIG. 7 is a flow diagram of a learning process according to one embodiment of the embodiment.

FIG. 7 shows a flowchart detailing a representative learning process 700 in accordance with the described embodiments. Process 700 can begin at 702 by tagging the ambient activity profile as recognized and at 704, associating the now recognized ambient activity profile with a workout template. For example, the now recognized ambient activity profile can be paired with that workout template associated with a genre of workouts corresponding to the recognized ambient activity profile. For example, if the genre of the recognized ambient activity profile is aerobic dance, then any of a number of available aerobic dance workout templates can be used. In any case, at 706, the recognized activity data profile database is updated to include the recognized ambient activity profile and the link to the associated workout template.

Figure 8:
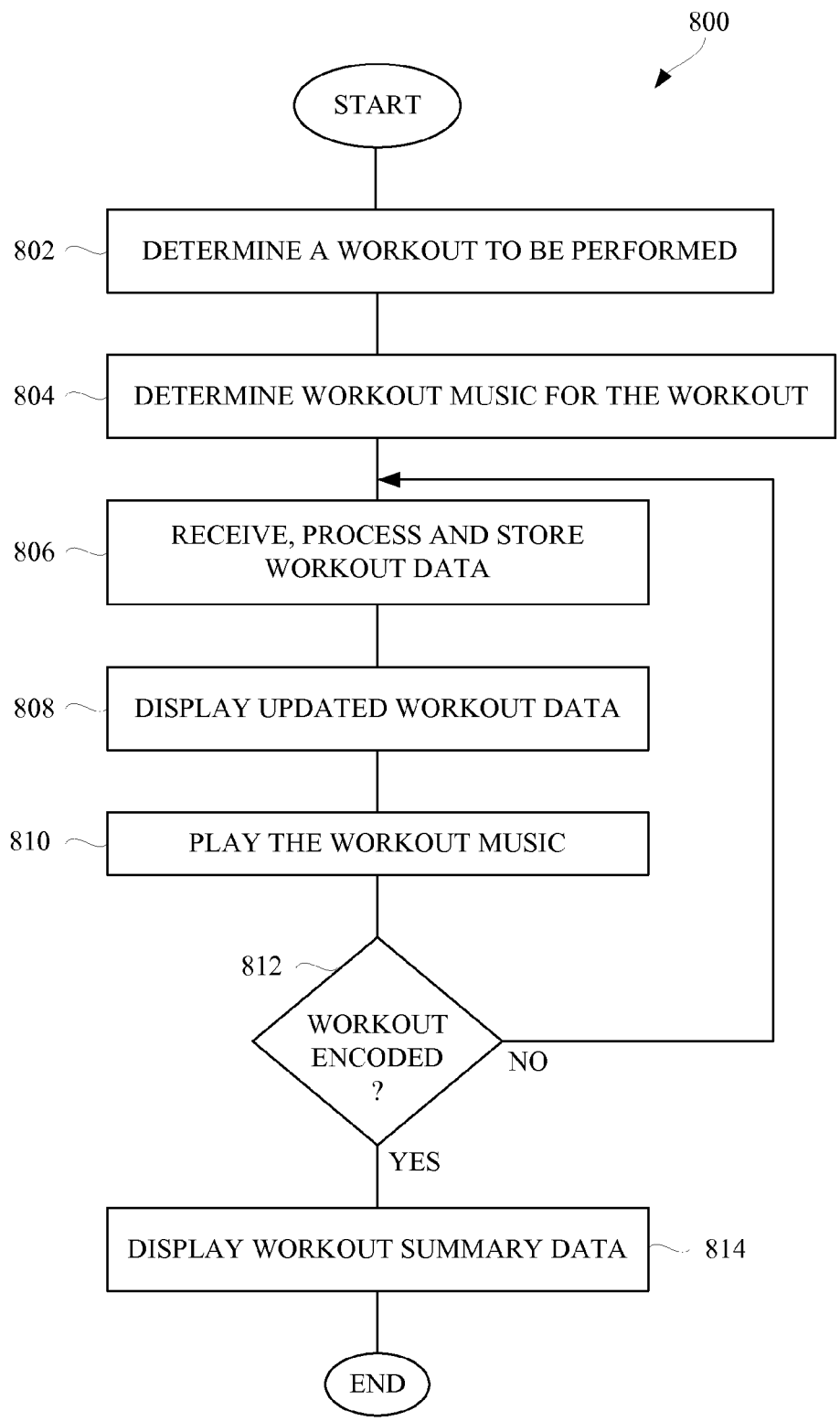
FIG. 8 is a flow diagram of a workout initiating process according to one embodiment of the embodiment.

FIG. 8 is a flow diagram of process 800 that can be used to initiate a workout session according to one embodiment. The process 800 is, for example, performed by a computing device, typically a portable computing device. For example, the computing device can be a personal media device, such as the personal media device 102 illustrated in FIG. 1.

Process 800 begins at 802 by determining a workout to be performed. The determination can be done manually by the user or it can be done in real time in the background without direct user intervention. For example, the determination 802 of the workout can include receiving a workout type indication and also receiving one or more workout characteristics for the workout. In other cases, however, the determination of the workout can be based upon ambient activity data, extrinsic factors such as location, time of day, and so forth. Nevertheless, after a workout has been determined 802, workout music for the workout is determined 804. The workout music is music that is played by the computing device (e.g., personal media device) during the workout. Next, as the workout is ongoing, workout data is received processed and stored 806 at the computing device. The workout data can, for example, be received from an activity device, such as sensor 104 illustrated in FIG. 1. In addition, updated workout data is displayed 808. Typically, the computing device includes a display device that is able to display workout data during the workout. In addition, the workout music is played 810 during the workout by the computing device. By playing the workout music, the workout can be enhanced by motivating the individual or otherwise entertaining the individual during the workout.

Next, a decision 812 determines whether the workout has ended. The workout can end in response to a user request or automatically based on a condition (e.g., time, distance, etc.). When the decision 812 determines that the workout has not ended, the workout process 800 returns to repeat the block 806 and subsequent blocks so that subsequent workout data can be received, processed and stored 806. Thereafter, the updated workout data can be displayed 808 and the workout music can continue to be played 810. Hence, the blocks 806-810 are performed during the workout such that (i) new workout data can be periodically captured, (ii) updated workout data can be periodically displayed, and (iii) the workout music can be continuously played throughout the workout. On the other hand, once the decision 812 determines that the workout has ended, the workout data no longer needs to be received, processed and stored. Instead, once the workout has ended, workout summary data is displayed 814. The workout summary data 814 displays data that summarizes the workout. The workout music may or may not automatically end at the end of the workout. Following the block 814, the workout process 800 ends.

Figure 9A:
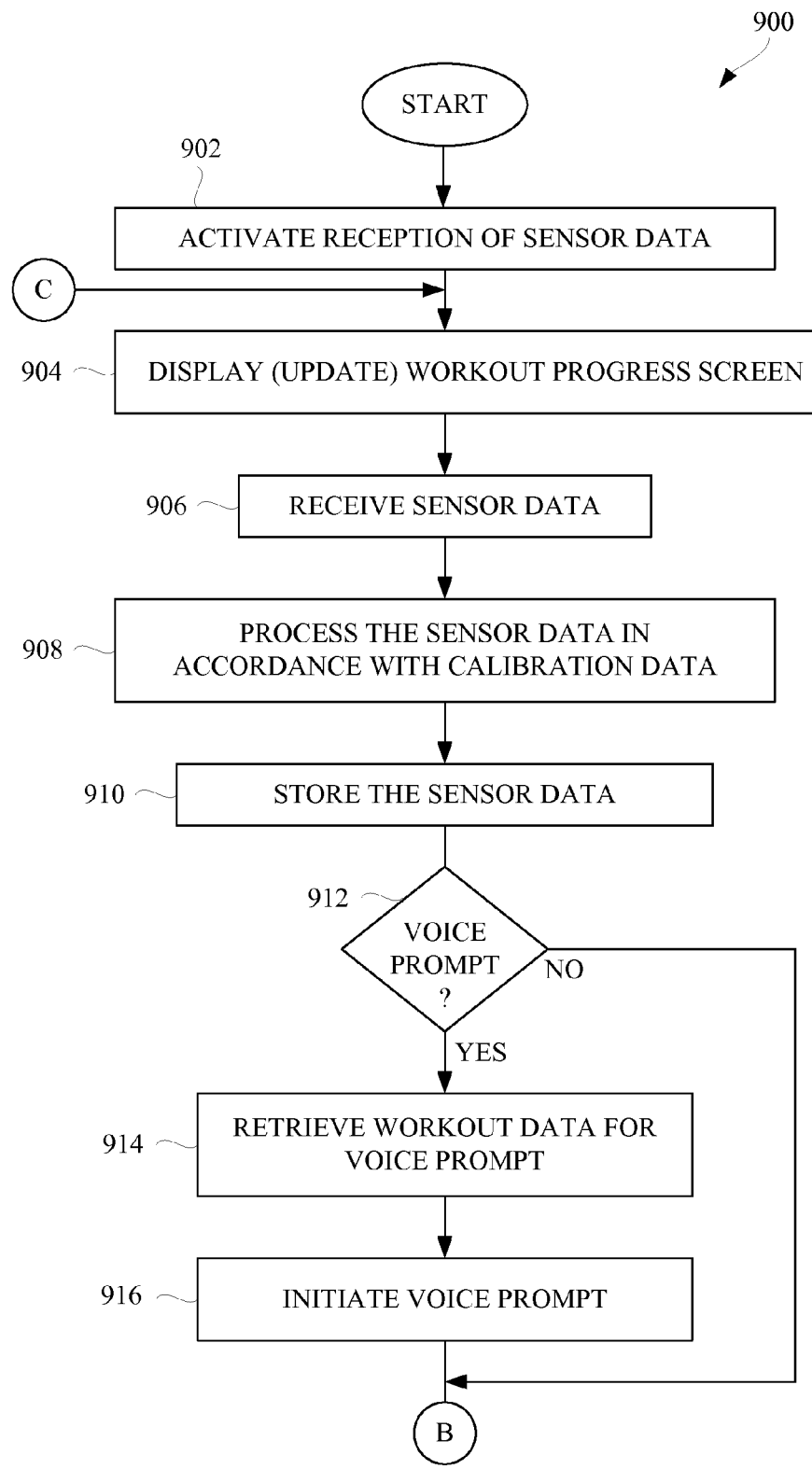
FIGS. 9A and 9B are flow diagrams of a workout manager process according to one embodiment of the embodiment.
Figure 9B:
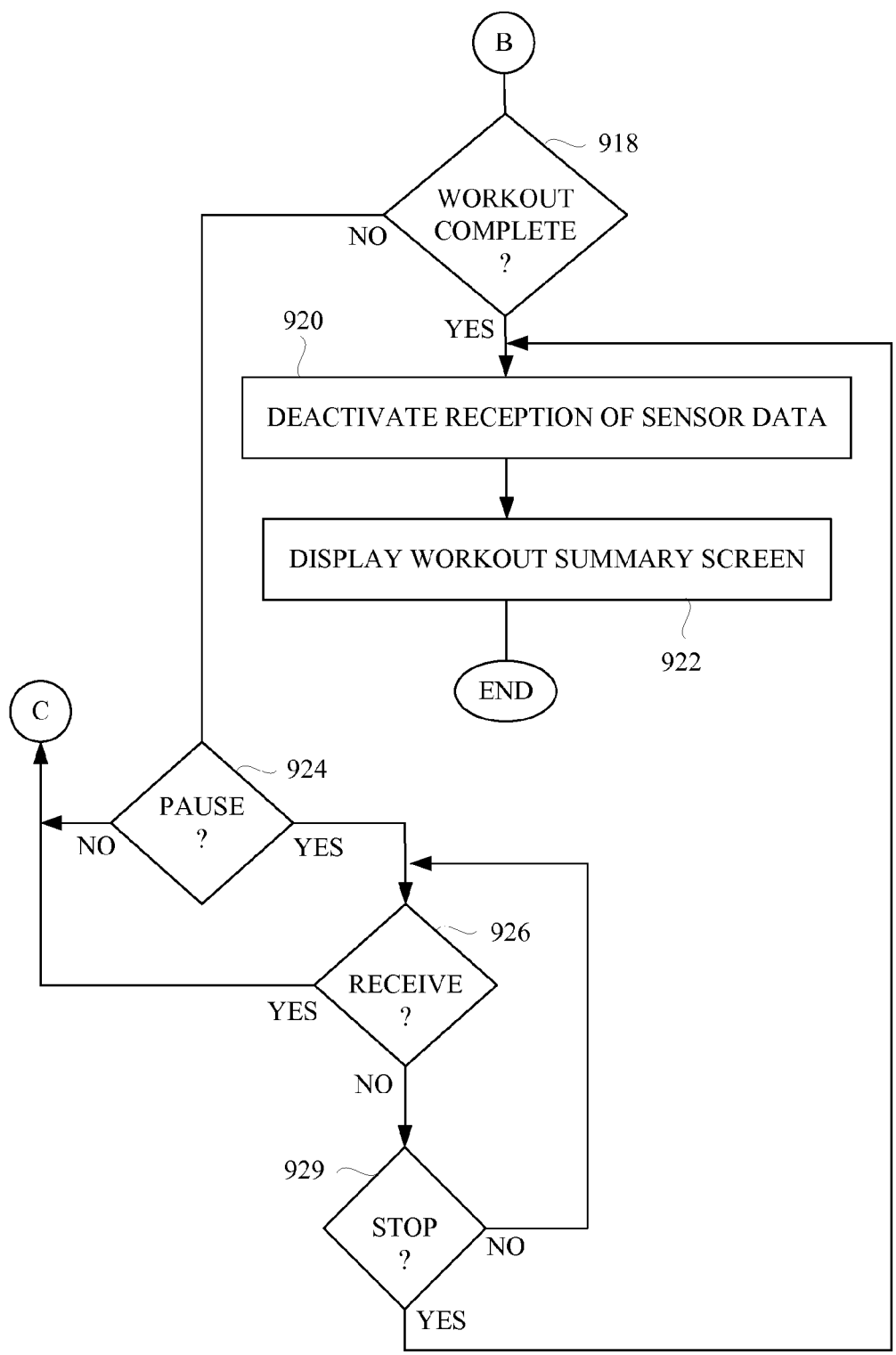

FIGS. 9A and 9B are flow diagrams of a workout manager process 900 according to one embodiment of the embodiment. The workout manager process 900 is associated with a workout manager that is a software module that operates to manage the capture, processing and storage of activity related data as well as displaying appropriate information and playing music to the user of the computing device (personal media device).

The workout manager process 900 at 902 activates reception of sensor data. The sensor data is, for example, data provided by a sensor within an activity device. For example, the activity device can be sensor 104 illustrated in FIG. 1. Next, a workout progress screen is displayed 904. The workout progress screen provides information to the user as to their progress through the workout. As the workout proceeds, sensor data is received 906. The sensor data is processed 908 in accordance with calibration data. The calibration data is data that is provided through a calibration process so that the sensor data can be better interpreted and thus more accurate in the determination of the user's progress with respect to the workout. The progress can be measured in a variety of different ways depending upon the application. In one exemplary application, the sensor data can be used to determine pace and distance traveled by a user during a workout. Hence, the calibration data can be used in such a case to more accurately determine the pace and distance for a workout. After the sensor data is processed 908, the sensor data is stored 910.

As the workout is ongoing, voice prompts can be provided to the user. Hence, a decision 912 determines whether a voice prompt is to be provided. When the decision 912 determines that a voice prompt is to be provided, workout data for the voice prompt is retrieved 914. Here, the voice prompt is to be associated with the workout that is ongoing. Hence, the voice prompt is associated with and provides to the user voice feedback pertaining to workout data. Next, the voice prompt is initiated 916. In one embodiment, the voice prompts are provided at predetermined points along a given type of workout. In another embodiment, the voice prompt can be provided based on performance metrics. For example, when the user runs his/her fastest mile the user can be provided with a voice prompt indicating that they have achieved a personal best. Here, the user can be congratulated for reaching a particular performance metric. Alternatively, when the decision 912 determines that a voice prompt is not to be provided, the blocks 914 and 916 can be bypassed.

Following the block 916 or its being bypassed, a decision 918 determines whether a workout is complete. When the decision 918 determines that the workout is complete, reception of sensor data is deactivated 920. Next, a workout summary screen is displayed 922. The workout summary screen provides a summary of the workout for the user. For example, in the case of a workout involving running, the workout summary can provide the user with information on total distance, total time, pace, etc. for the workout performed by the user. Following the block 922, the workout manager process 900 ends.

Alternatively, when the decision 918 determines that the workout is not complete, a decision 924 determines whether a pause has been requested. A user can pause a workout as they desire, such as through a user input action with respect to the computing device (personal media device). In any case, when the decision 924 determines that a pause has not been requested, the workout manager process 900 returns to repeat the block 904 and subsequent blocks so that the workout monitoring can continue, the workout progress screen can be updated, sensor data can be retrieved, processed and stored, and any voice prompts that are appropriate can be presented. Alternatively, when the decision 924 determines that a pause has been requested, a decision 926 determines whether the workout is to be resumed. That is, once the workout is paused, the user can resume the workout by another user interface interaction with the computing device. If the decision 926 determines that the workout has been resumed, the workout manager process 900 again returns to repeat the block 904 and subsequent blocks. On the other hand, when the decision 926 determines that the workout is not to be resumed, a decision 928 determines whether the workout is to be stopped. When the decision 928 determines that a workout is not to be stopped, the workout manager process 900 returns to repeat the decision 926 so that the workout can be resumed or stopped as requested by the user. Alternatively, when the decision 928 determines that the workout is to be stopped, the workout manager process 900 returns to repeat the block 920 and subsequent blocks so that the workout can be ended in its normal fashion.

The various aspects, embodiments, implementations or features of the embodiment can be used separately or in any combination. The described embodiments can be implemented by software, hardware or a combination of hardware and software. The described embodiments can also be embodied as computer readable code on a computer readable medium. The computer readable medium is any data storage device that can store data which can thereafter be read by a computer system. Examples of the computer readable medium include read-only memory, random-access memory, CD-ROMs, DVDs, magnetic tape, optical data storage devices, and carrier waves. The computer readable medium can also be distributed over network-coupled computer systems so that the computer readable code is stored and executed in a distributed fashion.

The many features and advantages of the described embodiments are apparent from the written description and, thus, it is intended by the appended claims to cover all such features and advantages of the embodiment. Further, since numerous modifications and changes will readily occur to those skilled in the art, the described embodiments should not be limited to the exact construction and operation as illustrated and described. Hence, all suitable modifications and equivalents may be resorted to as falling within the scope of the embodiment.

What is claimed is:

1. A method comprising:
   detecting, by a sensor of a system, ambient activity;
   generating, by a processor of the system, ambient activity data in accordance with the detected ambient activity by the sensor, the ambient activity data including physical ambient activity data;
   recognizing, by the processor, relevant ambient activity data from irrelevant ambient activity data by comparing the physical ambient activity data to a pattern of physical activity data;
   receiving, by the processor, a starting trigger, the starting trigger causing the processor to initiate a physical activity session;
   receiving physical activity data from the sensor during the physical activity session; and
   processing by the processor, the physical activity data and the recognized ambient activity data in a manner in accordance with the physical activity session.

2. The method as recited in claim 1, wherein at least one of the detecting, generating, receiving and processing is performed as a background operation of the system.

3. The method as recited in claim 1, wherein the starting trigger is a user-initiated event.

4. The method as recited in claim 1, wherein the starting trigger is a known pattern of ambient activity data that operates to start the physical activity session.

5. The method as recited in claim 1, further comprising;
receiving a stopping trigger, the stopping trigger causing the processor to stop processing the physical session activity data at least for a predetermined amount of time.

6. The method as recited in claim 1, further comprising
generating a data profile corresponding to the ambient activity data, comparing the data profile to at least one recognized activity data file, and tagging the data profile as recognized when the comparing indicates a match; and
storing at least some of the recognized ambient activity data in a data storage device.

7. A personal electronic device adapted for assisting a user during a physical activity session, comprising:
a processor; and
a sensor in communication with the sensor and arranged to detect an ambient activity and
provide corresponding ambient activity data to the processor, where the ambient activity data includes physical ambient activity data, and wherein the processor performs operations comprising:
recognizing relevant ambient activity data from irrelevant ambient activity data by comparing the physical ambient activity data to a pattern of physical activity data;
responding to a starting trigger by starting a physical activity session;
receiving physical activity data from the sensor during the physical activity session;
processing the physical activity data and the recognized ambient activity data in a manner in accordance with the physical activity session.

8. The personal electronic device as recited in claim 7, wherein at least one of the processor operations related to assisting the user during the physical activity session is a background operation.

9. The personal electronic device as recited in claim 7, wherein the sensor is an external circuit in wired communication with the processor.

10. The personal electronic device as recited in claim 7, wherein the sensor is an external circuit in wireless communication with the processor.

11. The personal electronic device as recited in claim 7, wherein the starting trigger is a user initiated event.

12. The personal electronic device as recited in claim 7, wherein the starting trigger is a known pattern of sensor data that operates to automatically start the physical activity session.

13. The personal electronic device as recited in claim 7, wherein the physical activity session is stopped by a stopping trigger, the stopping trigger based upon a condition.

14. The personal electronic device as recited in claim 7, wherein at least one of the operations of the processor with regards to the physical activity session is a background operation.

15. A non-transitory, computer readable medium for storing computer code executable by a processor in a personal electronic device comprising:
computer code for generating ambient activity data in accordance with the ambient activity detected by a sensor, where the ambient activity data includes physical ambient activity data;
computer code for recognizing relevant ambient activity data from the sensor from irrelevant ambient activity data by comparing the physical ambient activity data to a pattern of physical activity data;
computer code for triggering a physical activity session;
computer code for receiving physical activity data in accordance with the physical activity session; and
computer code for processing the recognized ambient activity data and the physical activity data from the sensor in a manner in accordance with the physical activity session.

16. The non-transitory, computer readable medium as recited in claim 15, wherein the starting trigger is a user-initiated event.

17. The non-transitory, computer readable medium as recited in claim 15, wherein the starting trigger is a known pattern of sensor data.

18. The non-transitory, computer readable medium as recited in claim 15, where the computer code for determining if the ambient activity data is recognized, comprises:
computer code for generating a data profile corresponding to the received ambient activity data;
computer code for comparing the data profile to at least one recognized activity data file; and
computer code for tagging the data profile as recognized when the comparing indicates a match.

19. A system, comprising:
a processor;
a data storage device; and
a sensor arranged to detect an ambient activity and provide corresponding ambient activity data to the processor, where the ambient activity data includes physical ambient activity data, and wherein the processor evaluates the ambient activity data to recognize relevant ambient activity data from irrelevant ambient activity data by comparing the physical ambient activity data to a pattern of physical activity data, wherein, in response to a starting trigger, the processor performs one or more operations that cause the system to initiate a physical activity session by processing physical activity data from the sensor and the recognized ambient activity data in accordance with the physical activity session.

20. The system as recited in claim 19, wherein when the trigger is a stopping trigger, the processor stops processing the physical activity data and the recognized ambient activity data for at least a pre-determined period of time.

21. The system as recited in claim 20, wherein the portable electronic device provides feedback to the user during the physical activity session, the feedback including workout music, voice prompts, and visual feedback.

22. The system as recited in claim 19, wherein at least one of the processor operations related to the physical activity session is a background operation.

23. The system as recited in claim 19, wherein the ambient activity data includes data that relates to a condition of a local environment at a geographic location of the system.

* * * * *

UNITED STATES PATENT AND TRADEMARK OFFICE
CERTIFICATE OF CORRECTION

PATENT NO. : 9,081,889 B2  
APPLICATION NO. : 12/943852  
DATED : July 14, 2015  
INVENTOR(S) : Ingrassia, Jr. et al.

Page 1 of 1

It is certified that error appears in the above-identified patent and that said Letters Patent is hereby corrected as shown below:

In the claims

Column 16, Line 65 Claim 1 delete "processing" and insert -- processing, --, therefor.

Column 17, Line 13 Claim 6 delete "comprising" and insert -- comprising: --, therefor.

Column 17, Line 36 Claim 7 after "session;" insert -- and --.

Column 18, Line 3 Claim 15 delete "device" and insert -- device, --, therefor.

Signed and Sealed this  
Sixteenth Day of August, 2016

Michelle K. Lee  
*Director of the United States Patent and Trademark Office*